United States Patent [19]

Averette

[11] Patent Number: 5,147,551
[45] Date of Patent: Sep. 15, 1992

[54] SOLIDS AND SEMI-SOLIDS SAMPLING APPARATUS, METHOD, AND FLUID INJECTION APPARATUS

[75] Inventor: Julius P. Averette, Baker, La.

[73] Assignee: Dynatech Precision Sampling Corporation, Baton Rouge, La.

[21] Appl. No.: 512,194

[22] Filed: Apr. 20, 1990

[51] Int. Cl.⁵ ............................................. B01D 15/00
[52] U.S. Cl. ..................................... 210/640; 210/472
[58] Field of Search .................... 422/61, 69, 100, 101, 422/102; 210/640, 472, 476, 664, 643

[56] References Cited

U.S. PATENT DOCUMENTS

3,859,209  1/1975  Jahnsen et al. ...................... 210/664
4,326,957  4/1982  Rosenberg ........................... 210/472

Primary Examiner—Frank Spear
Attorney, Agent, or Firm—Llewellyn A. Proctor

[57] ABSTRACT

Apparatus for processing solids and semi-solids specimens for the extraction therefrom of non-solids or fluid components for analysis. As a sub-assembly, the solids preparation and extraction device can be employed in combination with other sub-assemblies of an automated fluid injector which includes, or further includes, (B) a syringe, (C) an injector feed for introducing a fluid specimen into the syringe, and (D) a feed tray, magazine or carrousel for transporting fluid-specimen containing bottles, or vials for pick up of fluid therefrom by the injector feed assembly for delivery to the syringe. The apparatus embodiment also includes compartmented bottles, or vials, transportable via said feed tray to the solids preparation and extraction sub-assembly, within which a weighed amount of a solids or semi-solids specimen can be placed, crushed and the non-solids components thereof extracted, and removed; and also the process for extracting said non-solids component.

22 Claims, 3 Drawing Sheets

SOLIDS AND SEMI-SOLIDS SAMPLING APPARATUS, METHOD, AND FLUID INJECTION APPARATUS

1. FIELD OF THE INVENTION

This invention relates generally to automatic fluid injectors, or instruments, of the class used for sampling and analyzing fluid specimens, viz. gases and liquids. In particular, it relates to improvements in these devices which enable them to process solids and semi-solids specimens for the extraction therefrom of non-solids or fluids components for analysis.

2. BACKGROUND

Automated fluid injection devices, particularly automated needle syringes, have gained wide acceptance by industry and by the scientific and medical communities. This is because these devices are generally capable of dispensing very small, accurately measured quantities of fluid specimens on the order of a few microliters, generally a fractional part of a microliter up to about 50 microliters with high accuracy and precision. Moreover, the advantages offered by modern data gathering techniques, and consequent reduction in operating man power without loss in accuracy make these devices particularly useful in modern industrial establishments.

Typically, in the operation of an automated fluid injection device, septum covered bottles, or vials charged with a fluid specimen, are transported in seratim via a magazine to a station adjacent a probe assembly, a needle of the probe assembly is projected through the septum of a vial and employed as a conduit to convey a portion of the fluid specimen to the barrel of the syringe. The circuit through which the specimen is conducted, and barrel and needle of the syringe are cleaned, purged and a quantity of the fluid specimen is measured out and injected via the needle end of the syringe into the inlet of an analytical instrument, e.g., a G.C. or mass spectrometer.

Whereas these devices have proven admirably satisfactory in sampling and analyzing fluid specimens, viz. gases and liquids, and have replaced much of the earlier used technology for the sampling and analysis of fluid specimens, techniques and methods for the sampling and analysis of solids and semi-solids materials which contain volatiles components lag far behind. Innumerable hours are presently spent in the qualitative and quantitative analysis of solids and semi-solids materials, e.g., soil samples to determine the presence and content of non-solids, or fluids components. Moreover, e.g., tissues, exemplary of which are shrimp, fish, meat and orange peels, and plastics materials, are frequently analyzed for determination of the presence of various volatile, liquid or gas components. Present procedures almost, if not always, invariably require grinding up the solids or semi-solids specimen, washing the solids with a liquid to dissolve out the component for which the analysis is being made, clean up of the solution, and injection of the solution into an analytical instrument. Analysis of this type require a great deal of time, manipulations and close attention by a very skilled technician, or operative. Most want for accuracy, not on small part due to the difficulty of properly grinding up the specimen, but also due to the failure to completely extract with the solvent the component, or components, to be analyzed. There thus exists a need to provide better techniques for the qualitative and quantitative sampling of solids and semi-solids materials for analysis of their non-solids components.

3. OBJECTS

Accordingly, it is a primary objective of the present invention to satisfy this need, and others. Refinements presented herein provide an opportunity for improving the structure disclosed and claimed in my pending application Ser. No. 233,354, filed Aug. 18, 1988 extending its utility such that it becomes capable of processing for analysis not only fluid specimens, but additionally solids and semi-solids materials.

In particular, it is an object of this invention to provide an autosampler mechanism, or device, for the extraction, or removal of a non-solids or fluid component from a solid or semi-solids material for transfer to an analytic instrument for analysis.

A further, and more particular object of this invention is to provide apparatus for processing, suitably in automated fashion, weighed solids specimens in vials, or bottles, delivered in seriatim for the solvent extraction of non-solids or fluid components therefrom and delivery of the component, or components, taken from these specimens to an analytical instrument for analysis.

A yet more specific object is to provide a vial, or bottle, adapted for special use in the extraction, or removal of a non-solids or fluid component from a solid or semi-solids material; particularly in combination with apparatus for processing, suitably in automated fashion, weighed solids specimens as characterized.

It is also an object of this invention to provide a process for the extraction, and removal, of a non-solids or fluid specimen from a solid or semi-solids materials with accuracy and precision for transfer to an automatic fluid injector, or syringe, for injection into an analytical instrument.

4. THE INVENTION

These objects and others are achieved in accordance with the present invention embodying improvements in automatic fluid injectors to render these devices useful in processing for analysis fluids, or solids and semi-solids materials, or both. The automatic fluid injector differs from previous devices of this type, in that it provides an instrument not only capable of handling, or processing for analysis extremely small fluid specimens per se, but also for extracting, or removing, for analysis extremely small non-solids or fluids specimens from solids or semi-solids specimens. The solids or semi-solids specimens, while contained in compartmented bottles, or vials, are delivered by a feed tray, magazine or carrousel in seriatim, to a solids preparation and extraction station wherein the solids or semi-solids are crushed and ground, contacted directly with a solvent, heated and mixed to dissolve out the non-solids or fluid components from the solid or semi-solids material, the non-solids or fluid components contacted and vaporized, or otherwise dispersed, in a non-reactive gas, and the non-reactive gas containing the non-solids or fluid components is then injected into an analytical instrument, particularly a purge gas trap analyzer for subsequent analysis, e.g., in a gas chromatograph.

The compartmented bottles, or vials, delivered to the solids preparation and extraction station by the feed tray, magazine or carrousel, suitably are tubular members partitioned by a dividing frit, or selectively porous diaphragm, into two chambers or compartments; and the ends of the two chambers in the direction opposite the frit are closed with seals, each penetratable by hollow or tubular needles. A solid or semi-solid placed on one side of, e.g., atop the frit, or selectively porous diaphragm, can be crushed and ground, or otherwise pulverized, e.g., via an ultra sonic device, lazer, or stir device, a liquid solvent injected into the chamber containing the pulverized solid and contacted therewith, and the contents thereof heated to dissolve out the non-solids or fluids. A non-reactant gas, e.g., helium, can then be introduced via a hollow needle into the chamber on the opposite side of the frit, gas dispersed via the frit openings into the liquid solvent to vaporize out the non-solids or fluids components of the crushed, ground solid or semi-solids, and the gas then injected into an analytical instrument, or purge gas trap analyzer.

A solids preparation and extraction device lies at the heart of the present invention. This device is structured to receive, handle and process for analysis the solid or semi-solids containing compartmented bottles delivered in seriatim by the feed tray, magazine or carrousel. This device is programmable to select the appropriate solid or semi-solids containing compartmented bottles from a feed tray containing other bottles, or vials, which contain only fluids. In its preferred use therefore, the solids preparation and extraction device of this invention is employed as a sub-assembly or (A) a solids preparation and extraction station in combination with other sub-assemblies of an automated fluid injector which includes, or further includes, (B) a syringe, (C) an injector feed assembly for introducing a fluid specimen into the syringe, and (D) a feed tray, magazine or carrousel for transporting fluid-specimen containing bottles or vials for pick up of fluid therefrom by the injector feed assembly for delivery to the syringe as described, e.g., by U.S. application Ser. No. 233,354, supra. Non-solids specimens contained in vials, or bottles, carried by the magazine are programmed to bypass the (A) solids preparation and extraction station, and the specimens are processed in seriatim for delivery to an analytical instrument as fully described in the '354 application at Pages 8 through 26, and by FIGS. 1–16 of the drawings, herewith incorporated and made part of the present application by reference. The solid or semi-solids containing bottles, on the other hand, are serially processed on arrival at the (A) solids preparation and extraction station, on delivery thereto by (D) the feed tray, magazine, or carrousel. The liquid solvent, preheated if desired, is delivered to the chamber containing the pulverized solid, or semi-solids from any suitable container, or reservoir, and fed e.g., via a mechanical metering pump. Suitably, the syringe itself—which is not in use in processing a solid or semi-solids material—can be used for this purpose. The syringe in this instance would thus be used not in its normal capacity as a mechanism for injection of a fluid specimen to an analytical instrument, but to deliver the liquid solvent for contact with the crushed, ground solid or semi-solids component contained in the compartmented bottle for extraction of the non-solids or fluid component.

The invention, and its principle of operation, will be more fully understood by reference to the following detailed description of a specific and preferred embodiment, and to the attached drawings to which reference is made in the description. Similar numbers are used in the description to represent similar parts or components, and subscripts are used with numbers where parts or components are duplicated. Where reference is made in the written text to a component designated by the use of subscripts in the drawing, without reference to the subscripts, the designation is intended in a generic sense.

Reference is made, first generally to the figures which show a preferred solids preparation and extraction device. Quite clearly, as will be seen, this device can be independently mounted in an appropriate housing in the combination subsequently described and employed to process only solid or semi-solids solids specimens delivered on station thereto via a feed tray, magazine or carrousel. Conversely, it is clear that this device can be mounted in an appropriate housing with the additional sub-components (B) and (C), supra, to provide an instrument suitable for handling, on the same feed tray, magazine, or carrousel, bottles or vials which contain both (i) fluid specimens and (ii) solid or semi-solids specimens from which non-solids or fluid specimens can be extracted. A full and complete description of an automatic fluid injector for handling fluid containing vials, and its principal of operation, is given in the '354 application, supra. The present description will focus on a description of the principle of operation and function of a preferred solids preparation and extraction device, on a preferred type of compartmented bottle for use with this device, and process for carrying out this operation.

Figure 1:
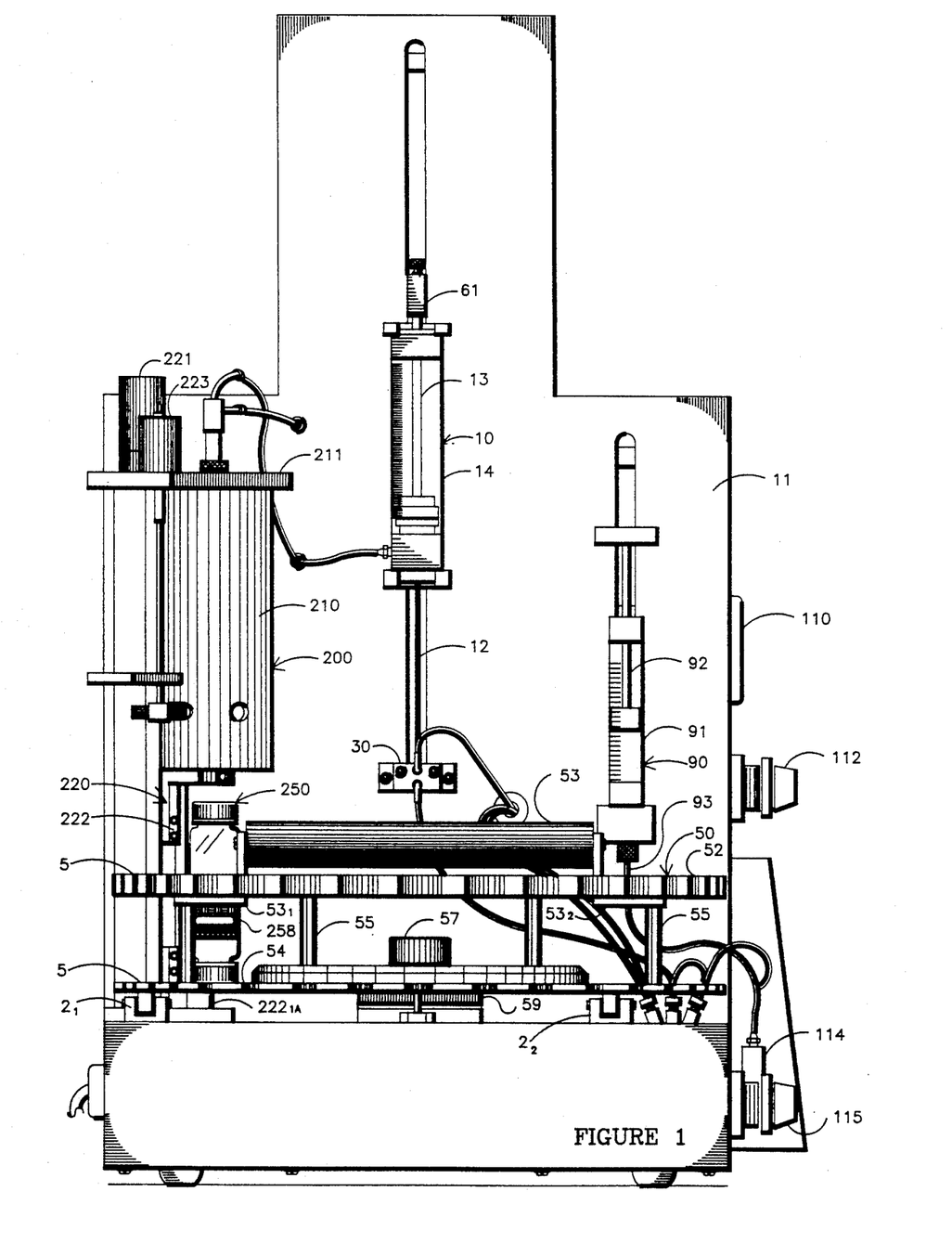
FIG. 1 depicts a left side elevation view of the instrument, this view showing, in particular, the location, position and relationship between the carrousel feed tray at the moment of its having delivered a solids-containing septum-sealed compartmented bottle of a series, the solids preparation and extraction mechanism at which the compartmented bottles, and others are stationed in sequential order on delivery by the carrousel feed tray for crushing and grinding the solid or semi-solids, the sample syringe from which, inter alia, hot liquid can be supplied for contact with the crushed solids, and an adjacent internal standards syringe.

Referring first directly to FIG. 1, the principle components of the instrument employed to extract and recover the non-solids or fluid components from a solid or semi-solids specimen, and inject said recovered components to an analytical unit, include a solids preparation and extraction sub-assembly 200, a syringe 10 and carrousel feed tray 50 mounted upon, and within a suitable housing. The feed tray 50 transports weighed specimens in bottles in programmed sequence, the compartmented bottles 250 containing the solids or semi-solids first to a position for operation thereon by the solids preparation and extraction assembly 200. On the other hand, bottles or vials which do not contain solid or semi-solids specimens are first stationed below (C) the injector feed assembly which is employed for introducing a fluid specimen into (B) the syringe 10 for injection via its dispersing or needle end to an analytical instrument as described in the '354 application. The sample syringe 10 is vertically mounted upon an outer support wall 11, with its dispensing end comprised of a pair of concentric hollow needles 12, viz., $12_1$, $12_2$ (not shown) projected vertically downwardly through an axial opening, or channel within a valve block 30. Block 30, as described in the '354 application, is suitably constituted of a plastic (e.g., Teflon) to provide a tight seal on the end of the concentric needle 12. It provides a means for loading the syringe 10 which is used for dispensing a fluid specimen to the inlet of an analytical instrument. A hole or port in the side of needle 12 "matches" with a hole or port in block 30. This allows a liquid specimen to be drawn into the syringe 10. Bubbles and foam are eliminated because the liquid specimen is "pushed" into the syringe under pressure, and not drawn in by a vacuum. It is very important that no bubbles enter the syringe 10 as it is being filled; since this would directly adversely affect the volume of the specimen measured out and delivered by the syringe.

Septum covered liquid-specimen filled vials (not shown) are thus delivered in seriatim via rotatable carrousel feed tray 50 to a position below the valve block 30 for pick up of a fluid specimen from a vial (not shown) by action of the concentric hollow needles 12 (not shown) of the sample syringe 10. The upper terminal end of the plunger rod 13 is affixed to an end of a sample syringe plunger drive 61, which is integral and movable with a plate (not shown) carried upon a threaded linear motor shaft (not shown) reciprocably driven by a motor (not shown). The plunger rod 13 is thus reciprocably vertically movable within the barrel 14 of the syringe 10, while the syringe 10 is held in relatively fixed position, via actuation of the motor, the limit of movement being defined by an upper, and lower, microswitches, both of which are mounted (with oppositely faced contact ends) upon plate $61_1$ not shown). The body of the syringe 10 is secured at its lower end to a bottom syringe mount plate, movable upon and carried by threaded linear motor shaft driven by a second motor (not shown). The pair of concentric needles 12 of the syringe 10 can thus be thrust downwardly through the vertically aligned opening through valve block 30 to project the needles 12 into a fluid containing vial, and subsequently raised into the valve block 30 to purge the initial liquid of foam, or bubbles, and the liquid specimen then injected. The details of construction, the drive mechanism, and the operation and function of the syringe 10 is described in detail at Pages 13 through 19 of the '354 application.

In operation of the solids preparation and extraction sub-assembly however, the syringe 10 serves a dual purpose in that it supplies a solvent for contact with the crushed, ground solid or semi-solids specimen. The instrument further includes, as does that disclosed in the '354 application, an auxillary, or standard syringe 90 inclusive of a barrel 91, a plunger rod 92 reciprocably mounted within the upper end thereof, and a cannula, or needle 93 affixed within the lower end of the barrel. The upper, or handle end of the plunger rod 92 is affixed to a side of a plunger drive (not shown) which in turn is integrally mounted upon a plate carried by a threaded linear motor shaft (not shown) which is reciprocably driven by a motor (not shown). The instrument further includes various auxillary components located within the walls and floor of a housing inclusive generally of a blank/wash water gauge 110, waste water bottle (not shown), blank/wash water regulator 112, wash bottle (not shown), rotary valve 114, vial pressure regulator 115, vial pressure gauge (not shown), drive motor (not shown) for the carrousel feed tray 50, and a keyboard display (not shown). These several components and sub-assemblies are responsive to automatic control means not per se a feature of this invention.

The details of construction, the drive mechanism, and the operation and function of the standard syringe 90 is described in detail at Pages 19 through 21 of the '354 application.

The function of the carrousel feed tray 50, in processing septum covered fluid-specimen containing vials as described at Pages 21 and 22 of the '354 application, is to transport these vials (not shown) in seriatim to a location below the valve block 30. Vials used for this service contain a single compartment, or fill space. They are of an open screw top type enclosed by an elastomeric septum held atop a vial by an open centered cap threadably engaged to the neck of a vial, for pressurization of the liquid specimen contents with a gas, e.g., helium. The contents of a vial are removed by action of the needles 12 as generally previously described; or as detailed in the '354 application. Suitably, the carrousel feed tray 50 includes a tray comprised of an upper sample tray holder 52 to which is attached a tray handle 53 mounted via brackets $53_1$, $53_2$ to the tray holder, and a sample tray base 54 separated by stand offs 55 providing a unitary tray assembly. On the top of the tray holder 52 is provided a sample tray number retainer ring overlay, not shown. The composite feed tray mounted upon a sample tray spindle 57 at the geometric center of the instrument floor, and rotated via a motor (not shown) linked with the tray via a ring gear assembly 59. The tray, which rests upon tray wheels $2_1$, $2_2$, introduces the vials in consecutive order to a position below the valve block 30 for pick up of a fluid specimen therefrom via action of the sample syringe 10.

The carrousel feed tray 50 provides seating locations for both fluid-specimen bottles, or vials, and solid or semi-solids filled compartmented bottles, or vials, in any programmed order as desired for analysis. The circumferential edges of the upper sample tray holder 52 and tray base 54 of the carrousel feed tray 50 within which the bottles or vials are placed are slotted, or cut away providing slots 5 which permit ready access for lifting compartmented bottles filled with solid or semi-solids material for processing, and extraction of non-solid components for analysis. The details of construction, and operation and function of the solids preparation and extraction sub-assembly 250, and a preferred type of compartmented bottle use in conjunction therewith, are hereafter described in detail by reference to FIGS. 1 through 4. For ease of illustration a single compartment bottle 250 of a preferred design is shown upon, and transported by the carrousel feed tray 50. The construction, and function of this compartmented bottle 250, since it aids in understanding the solids preparation and extraction sub-assembly, its function, and operation, it will be first described in some detail.

Figure 4:
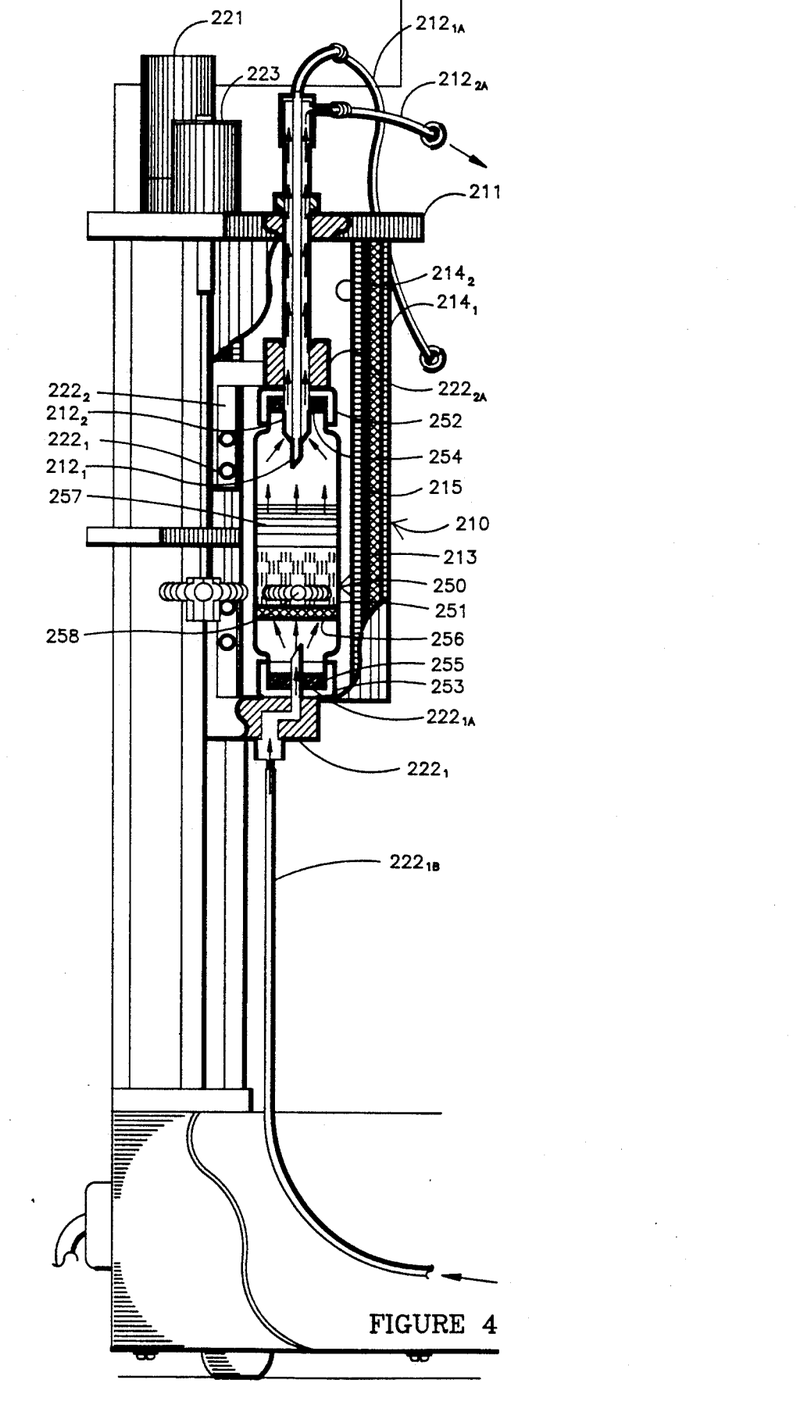
FIG. 4, taken with FIGS. 1–4 describe a cycle of operation beginning with the delivery and positioning of a solids-containing septum sealed compartmented bottle at the solids preparation and extraction station through the extraction and injection of a non-solids or fluid component to, e.g., a purge gas trap analyzer.

The compartmented bottle 250 is formed by an enclosing side wall 251, the two ends—both top and bottom—of which are adapted for sealing engagement with open-centered, septum-covered end caps. Preferably, the two ends are of reduced diameter and threaded for threadable engagement with open-centered, septum-covered screw type caps 252, 253. Suitably, the two smaller diameter ends of the bottle are externally threaded, and the inside opening of the caps 252, 253 are internally threaded for threaded engagement. Each of the central openings within the caps 252, 253 is covered with a septum 254, 255 to provide an impervious gas seal. With the sealed, septum-containing caps 252, 253 threadably engaged upon the two ends of the bottle 250, the bottle is separated into two compartments by a member selectively permeable to the flow of gas therethrough, but impermeable to the flow of liquid therethrough, suitably a partitioning frit 256; a member which contains pore size openings of diameter sufficiently large to permit the flow of gas therethrough, but (insufficient in diameter or) sufficiently small to prevent the passage of a liquid solvent therethrough. For example, a frit 256 which contains pore size opening of average diameter ranging from about 2 microns to about 30 microns, preferably from about 10 microns to about 20 microns, will prevent the flow of an aqueous liquid 257, e.g., water, downwardly through the frit. On the other hand, pore size openings of this size are sufficiently large to permit the flow of a gas, e.g., helium, upwardly through the frit at moderately low rates, e.g., at rates ranging from about 10 cubic centimeters (cc)/minute (min) to about 100 cc/min, preferably from about 30 cc/min to about 50 cc/min psi. In a preferred embodiment, as will subsequently be described, a magnetic stirrer device is employed to crush, and grind the solid or semi-solids specimen by rotation of the magnetic stir bar 258 placed atop or on the upper placed atop or on the upper face of the frit 256 to release the non-solids component, or fluid, for dispersal or solution within the solvent 257. Gas, e.g., helium injected into the lower compartment via the tubular needle $222_{1A}$ will thus ascend through the pores of the frit 256, strip out, evaporate and pick up the component dissolved or otherwise removed from the crushed, ground solid and convey the component via the annular passageway of the concentric needle $212_2$, and line $212_{2A}$, to the analytical instrument (FIG. 4).

The solids preparation and extraction subassembly 200, as shown by any of FIGS. 1-4, includes generally an electrical heater, or oven 210, and an elevator assembly 220 constituted of an upper carriage section $222_2$ and a lower carriage section $222_1$. It further includes an elevator motor 221 for raising and lowering the elevator assembly 220, and a stir motor 223 for inductive rotation of the magnetic stir bar 258. The electric oven 210, which is secured in place in fixed position upon a generally upright frame structure, or housing, below the plate 211 is constituted of an electric heating element-containing wall, to which current is supplied via electrical leads (not shown) surrounding an open space within which the elevator carriage 222, supported upon a generally upright frame structure, or housing, and carrying a compartmented bottle 250 within which a solution in contact with a solid or semi-solids specimen can be contained, can be raised, housed and heated. The electrical heating element 213, it will be observed is located between side walls $214_1$, $214_2$ of the heater, and on one side thereof is provided insulation 215. Within the plate 211 is provided an opening or aperture through which a pair of concentrically mounted needles 212 is projected, and rigidly retained in fixed vertical position. The inner needle $212_1$ is connected via a line $212_{1A}$ through which a liquid solvent, suitably a preheated liquid solvent if desired, can be introduced. The outer needle $212_2$ is connected via an outlet line $212_{2A}$, providing an annulus through which gas from the headspace above the level of the liquid in bottle 250 can be passed. The elevator assembly 220 is constituted of a carriage 222 provided with a lower elevator section $222_1$ and upper elevator section $222_2$ slidably mounted in a vertical groove (not shown) for upward and downward movement. The lower elevator section $222_1$ is provided with a needle $222_{1A}$ provided with a line $222_{1B}$ through which a gas can be injected. The upper elevator section $222_2$ is provided with a bottle guide $222_{2A}$ against the lower face of which the top of a bottle 250 can be pressed and stabilized. The elevator carriage 222 is driven upwardly and downwardly, as required, by the elevator motor 221 the shaft (not shown) of which is geared thereto via a mechanism (not shown). Activation of the stir motor 223 when the elevator carriage 222 is in raised position produces rotation of the magnetic stir bar 258 to crush and grind the weighed solid or semi-solids specimen contained in a compartmented bottle 250, and stir the liquid and solids content thereof.

A complete cycle of operation, beginning with a reference to FIG. 1, can be described as follows: In FIG. 1, the elevator carriage 222 is shown in its extreme downward position. The needle $222_{1A}$ through which a non-reactive gas, e.g., helium, can be injected is poised below the septum sealed open-centered cap 253 of bottle 250 having been so positioned by the carrousel feed tray 50. The lower compartment of the bottle 250 is dry and empty. The upper compartment of the bottle 250 contains, resting atop the frit 256, a magnetic stirrer bar 258 and a weighed portion of a dry solid or semi-solids material from which a non-solids component or fluid is to be extracted. The cap 252 closing the upper end of the bottle 250 lies in a position below the bottle guide $222_{2A}$. The cap 253 closing the lower end of the bottle 250 rests against the upper face of the tray base 54 above a notch 5. Its septum-sealed center is aligned with a notch 5 and the point, or tip of the upwardly projecting needle $222_{1A}$.

Figure 2:
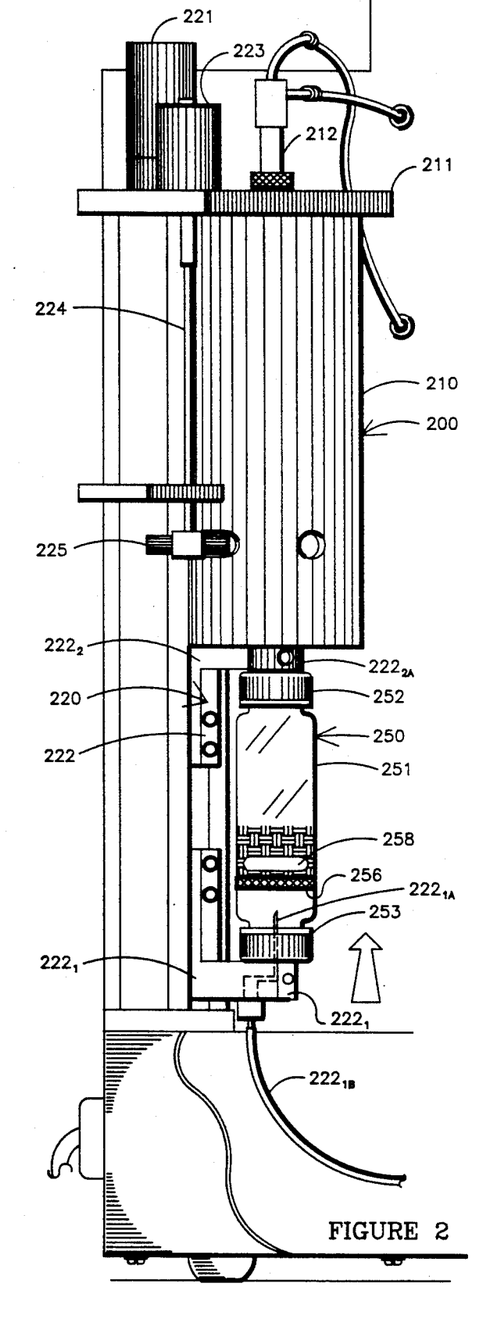
FIG. 2 depicts in some detail a solids-containing septum sealed compartmented bottle, and the solids preparation and extraction mechanism.

Referring to FIG. 2, the elevator is raised via activation of elevator motor 221. The sharp point of the needle of $222_{1A}$, as the elevator carriage 222 is lifted, is thrust through the open center of cap 253 and septum 255 coming to rest within the lower compartment of bottle 250. The lower, or bottom end of the bottle 250 now rests upon, and is supported on the upper side of the lower elevator section $222_1$. The upper end of the bottle 250, or cap 252 is now pressed within the downwardly directed concave face of the bottle guide $222_{2A}$, the bottle 250 now being aligned and stabilized.

Figure 3:
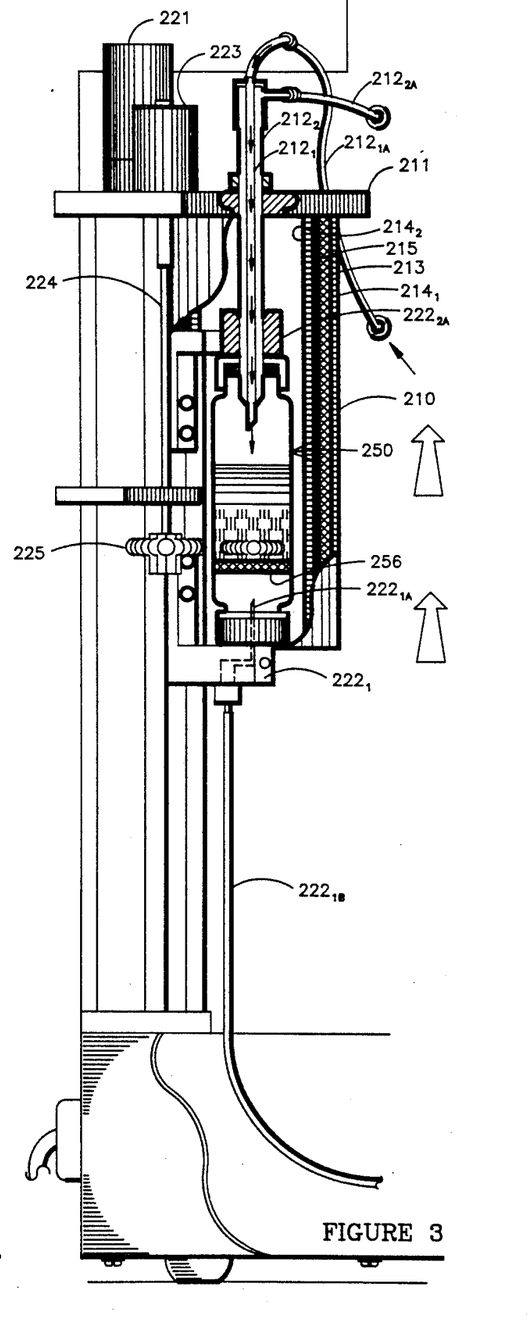
FIG. 3 depicts the solids preparation and extraction mechanism.

The elevator carriage 222, as shown by reference to FIG. 3, is now lifted to its maximum upward position, being driven to this position by continued activation of the elevator motor 221. As the elevator is lifted the septum 254 of bottle 250 is penetrated by the concentrically mounted pair of needles 212. On reaching its maximum upward position, the liquid solvent, e.g., water, is injected via line $222_2$ and inner tubular needle $212_1$ into the upper compartment of the bottle 250 to raise the level of the liquid up to but not exceeding a predetermined level. Now, the stir motor 223 is activated. The magnetic element 225, located on the end of the stir motor shaft 224 is thus rotated thereby inducing rotation of the magnetic stir bar 258. Rotation of the stir bar 258, located on the upper face of the frit 256, is continued for a time sufficient to crush and grind the solid or semi-solids material, releasing and extracting the non-solids or fluid components therefrom. The aqueous liquid is maintained within the upper compartment of bottle 250; being unable to pass through the small pore size openings of the frit 256.

Referring to FIG. 4, a non-reactive or inert gas, e.g., helium, is input via line $221_{1B}$ and needle $222_{1A}$ into the lower, dry compartment of bottle 250. The frit 256 acts as a distributor for the gas over its entire area, the gas ascending via the pore openings of the frit into the upper compartment of the bottle 250. Suitably, when the liquid solvent is added to the upper compartment of the bottle 250, gas flow via line $222_{1B}$ and needle $222_{1A}$ is initiated to flow through the frit 256 and the solvent-solids mixture simultaneously, while stirring. Rotation of the magnetic stir bar 258 is continued as the gas passes upwardly partially as very fine bubbles, through the stirred slurry of water and finely divided solids. There is no channeling of the gas, as occurs in many of the previous gas-solids extraction systems, and the pick up of non-solids or fluid components, particularly volatile organic contaminants as may be contained in, e.g., a soil sample, released from the solids or semi-solids materials is virtually complete. The vapors are removed from the upper compartment of the bottle 250 via the annular passageway located between the outside wall face of needle $212_1$, and the inside wall face of needle $212_2$, and passed via line $212_{2A}$ to a sample concentrator, or directly to an analytical instrument. Preferably, the specimen is passed to a packed column, generally referred to as a "trap". (The trap is part of a sample concentrator.) Upon completion of the flow through the purge cycle, gas flow through the trap is reversed and, e.g., the volatile organic contaminants held by the trap are carried to an analytical instrument, e.g., a gas chromatograph or mass spectrometer.

The cycle begins anew with return of the elevator carriage 222 to its downward position, and the delivery of a new bottle or vial, by the carrousel feed tray 50 as depicted by reference to FIG. 1.

It is apparent that various modifications and changes can be made without departing the spirit and scope of the present invention. The apparatus is constructed of materials substantially inert or non-reactive to the chemical or corrosive action of the solids, semi-solids or fluid components contained within the specimens handled. The bottle, or vials, are normally constructed of a clear plastic, or glass and the caps used therewith of a hard plastic or plastic-like material. The septum, and sealing components of the bottles, or vials, and as well the tubing used in the instrument are normally constructed of rubber or plastic, and the rest of the instrument of various metals.

The seals are preferably formed of a rigid or semi-rigid, resilient form of plastic or plastic-like material. The self-lubricated plastics are especially preferred in this capacity, and can also be applied as a laminate or protective film. The polyfluorinated ethylene polymers, notable among which is polytetrafluoroethylene (Teflon), are particularly outstanding. Conventional resilient or plastic-like materials, such as natural or synthetic rubbers can also be employed.

The carrousel feed tray, the solids preparation and extraction sub-assembly, the housing and various other components of the instrument is constructed of conventional metals, e.g., ferrous metals such as iron, iron alloys, steel, stainless steels, and the like; or such metals as aluminum, magnesium, brass, copper, bronze, chrome, alloys of these and other metals, and the like.

It is apparent that various changes, such as in the absolute or relative dimensions of the parts, materials used, and the like, as well as the suggested mode or particular sequence of operations, can be made without departing the spirit and scope of the invention, as will be apparent to those skilled in this art.

Having described the invention, what is claimed is:

1. Apparatus for the liquid extraction and separation for analysis of a non-solids component, or components, from a solid or semi-solids specimen via the use of a bottle with two open ends each of which is closed and sealed by an open-centered septum-covered cap, compartmented to provide a first compartment separated from an adjoining second compartment by a partitioning member selectively permeable to the flow of gas from said second compartment, but impermeable to the flow of liquid from said first compartment to said second compartment, the first compartment being adapted for the receipt of a weighed portion of said solid or semi-solids specimen, for receiving liquid, and expelling gases via its covering open-centered septum-covered cap, with said second compartment being adapted for receiving gas via its covering open-centered septum-covered cap, and expelling gases via the gas-liquid selective partitioning member into said first compartment, which comprises a generally upright frame structure, inclusive of an abuttment which carries a first tubular needle through which a liquid can be delivered to the first compartment of said compartmented bottle on insertion of said first tubular needle through the open-centered septum-covered cap of said first compartment, and a second tubular needle through which gas can be exhausted from said first compartment, an elevator mounted upon said upright structure, said elevator including an elevator carriage which carries a tubular needle through which a gas can be delivered to said second compartment via insertion of said tubular needle through the open-centered septum cap of said second compartment and distributed via the selectively gas-liquid permeable member into the first compartment for contact with the solids or semi-solids, vertically movable upwardly and downwardly upon said upright frame structure, a motor means for driving said elevator, and elevator carriage, upwardly and downwardly upon said generally upright frame structure, a heater provided with a side wall surrounding an enclosure within which the elevator carriage with a transported compartmented bottle can be withdrawn, and a means for crushing and grinding the weighed solid or semi-solids specimen carried within the first compartment of said compartmented bottle to facilitate dispersal of the solids or semi-solids specimen within the liquid supplied to said first compartment, pick up the non-solids component, or components, by the gas entering said first compartment from the second compartment, and dispersal of said non-solids component, or components, for analysis via ejection of the gas through the second tubular needle carried by the frame structure abuttment.

2. The apparatus of claim 1 wherein the frame structure is located on an instrument housing on which is mounted a feed tray for delivery of the compartmented bottle to the elevator for pick up.

3. The apparatus of claim 2 wherein the feed tray is of the carrousel type, and contains a plurality of compartmented bottles for processing in seriatim.

4. The apparatus of claim 1 wherein the tubular needles located upon the abuttment of the upright frame structure through which liquid can be delivered and gas exhausted, respectively, are concentrically mounted.

5. The apparatus of claim 4 wherein the inside needle of the pair of concentrically mounted pair of needles is adapted for delivery of a liquid, and the other for the exhaust of gas.

6. The apparatus of claim 1 wherein the lower portion of the elevator carriage of the elevator assembly carries the tubular needle to which a gas can be admitted.

7. The apparatus of claim 1 wherein the enclosing side wall of the heater contains electric resistance elements which are electrically heated.

8. The apparatus of claim 1 wherein the means for crushing and grinding a solid or semi-solids specimen contained within the first compartment of the compartmented bottle is a magnetic stirrer operative upon a magnetic stir bar contained within said first compartment.

9. In apparatus for the liquid extraction and separation for analysis of a non-solids component, or components, from a solid or semi-solids specimen via the use of one or more bottles, each of which is characterized as having two open ends sealed by an open-centered septum-covered cap, compartmented to provide a first compartment separated from an adjoining second compartment by a partitioning member selectively permeable to a flow of gas from said second compartment, but impermeable to a flow of liquid from said first compartment to said second compartment, said second compartment being adapted for receiving gas via its covering open-centered septum-covered cap, and expelling gas via the gas-liquid selective partitioning member into said first compartment, with said first compartment being adapted for the receipt of a weighed portion of said solids or semi-solids specimen, for receiving liquid for contact with said particulate solids or semi-solids specimen to extract said non-solids component, or components, and contact of said liquid-solids dispersed mixture with gas from said second compartment for the pick up of said non-solids component, or components therefrom, and expelling the gas via its open-centered septum covered cap for analysis, the combination comprising a housing, an upright frame structure mounted upon said housing, said upright frame structure including an abuttment which carries a first tubular needle through which a liquid can be delivered to the first compartment of said compartmented bottle on insertion of said first tubular needle through the open-centered septum-covered cap of said first compartment, and a second tubular needle through which gas can be exhausted from said first compartment, an elevator mounted upon said generally upright frame structure, the elevator including an elevator carriage, a lower portion of which carries a tubular needle through which a gas can be delivered to said second compartment via insertion of said tubular needle through the open-centered septum cap of said second compartment and distributed via the selectively gas-liquid permeable member into the first compartment for contact with the solids or semi-solids, vertically movable upwardly and downwardly upon said upright frame structure, a motor means for driving said elevator, and elevator carriage, upwardly and downwardly upon said generally upright frame structure, a carrousel feed tray rotatably mounted upon said housing for carrying said compartmented bottles for pick up by said elevator, a motor means for driving said carrousel feed tray, and a means for crushing and grinding a weighed solid or semi-solids specimen carried within the first compartment of said compartmented bottle to facilitate dispersal of the solids or semi-solids specimen within the liquid supplied to said first compartment, pick up the non-solids component, or components, by the gas entering said first compartment from the second compartment, and dispersal of said non-solids component, or components, for analysis via ejection of the gas through the second tubular needle carried by the frame structure abuttment.

10. The apparatus of claim 9 wherein the means for crushing and grinding a solid or semi-solids specimen contained within the first compartment of the compartmented bottle is a magnetic stirrer operative upon a magnetic stir bar contained within said first compartment.

11. The apparatus of claim 9 wherein within the housing is further included a syringe inclusive of a barrel into which a fluid specimen can be loaded, a needle mounted on an end of the barrel, and means for the displacement of the fluid specimen from said barrel via the dispensing end of the syringe to an analytical instrument, or via the tubular needle located within the abuttment of the upright frame structure to the first compartment of the compartmented bottle.

12. The apparatus of claim 9 wherein within the housing is further included an injector feed assembly comprised of a probe sub-assembly inclusive of a pair of hollow needles for the pick up of fluid specimen from a bottle carried by the carrousel feed tray for filling the barrel of said syringe.

13. The apparatus of claim 9 wherein within the housing is further included a syringe inclusive of a barrel into which a fluid specimen can be loaded, a needle mounted on one end of the barrel, and means for the displacement of the fluid specimen from said barrel via the dispensing end of the syringe to an analytical instrument, or via the tubular needle located within the abuttment of the upright frame structure to the first compartment of the compartmented bottle, and an injector feed assembly comprised of a probe sub-assembly inclusive of a pair of hollow needles for the pick up of fluid specimen from a bottle carried by the carrousel feed tray for filling the barrel of said syringe.

14. Apparatus, characterized as a compartmented bottle useful for the liquid extraction for analysis of a non-solids component, or components, from a solid or semi-solids material contained within a compartment, and for the pick up and removal from said compartment of the extracted component with a gas, which comprises an enclosing side wall, open-centered, septum-covered end caps adapted for sealing engagement with and covering each end of said enclosing side wall, sealing off the interior of the bottle within the confines of the enclosing side wall, a frit disposed across the side wall between its two ends to partition the interior of the bottle into compartments, the frit containing pore sizes of diameter sufficient to permit the passage of a gas from one compartment to the adjacent compartment which contains the solid or semi-solids material but insufficient to permit the passage of liquid from the compartment containing the solid or semi-solids material to the adjacent compartment, at rates ranging from about 10 cc/min. to about 100 cc/min.

15. The apparatus of claim 14 wherein the two ends of the enclosing side wall which forms the bottle are threaded, and each of the open-centered, septum-covered end caps are adapted for threadable engagement therewith.

16. The apparatus of claim 15 wherein the two ends of the enclosing side wall is of reduced diameter and externally threaded, and the open-centered, septum-covered end caps are internally threaded.

17. The apparatus of claim 14 wherein the pore size openings of the frit are of average diameter ranging from about 2 microns to about 30 microns.

18. The apparatus of claim 17 wherein the average pore size diameter of the frit openings ranges from about 10 microns to about 20 microns.

19. Apparatus, characterized as a compartmented bottle useful for the liquid extracting for analysis of a non-solids component, or components, from a solid or semi-solids material contained within a compartment, and for the pick up and removal from said compartment of the extracted component with a gas, which comprises an enclosing side wall of tubular shape, the two ends of which are of reduced diameter as contrasted with the mid portion of the tube, and externally threaded, open-centered, septum-covered end caps, internally threaded for threadable engagement with the external threads located at the two ends of the enclosing side wall, these sealing off the interior of the bottle within the enclosing side wall, a frit disposed across the side wall between its two externally threaded ends to partition the interior of the bottle into two compartments, the frit containing pore sizes of diameter sufficient to permit the passage of a gas from one compartment to the adjacent compartment which contains the solid or semi-solids material but insufficient to permit the passage of liquid from the compartment containing the solid or semi-solids material to the adjacent compartment, at rates ranging from about 10 cc/min. to about 100 cc/min.

20. The apparatus of claim 19 wherein the two ends of the enclosing side wall which forms the bottle are threaded, and each of the open-centered, septum-covered end caps are adapted for threadable engagement therewith.

21. The apparatus of claim 20 wherein the two ends of the enclosing side wall is of reduced diameter and externally threaded, and the open-centered, septum-covered end caps are internally threaded.

22. In a process for the liquid extraction and separation for analysis of a non-solids component, or components, from a solid or semi-solids material by crushing and grinding said solid or semi-solids material, contacting said particulate solid or semi-solids material with a liquid to extract said non-solids component, or components, and then further contacting said liquid-dispersed solids mixture with a gas for the pick up and removal of said non-solids component, therefrom for analysis, the improvement comprising conducting said solids grinding, liquid contacting and extraction steps in a first zone separated from a second zone by a member selectively permeable to the flow of gas therethrough but impermeable to the flow of liquid therethrough, and subsequently passing the gas from the second zone through said selectively permeable member to pick up and remove for analysis the non-solids component, or components, from the liquid-dispersed solids mixture.

* * * * *